(12) United States Patent
McLaughlin et al.

(10) Patent No.: US 11,328,817 B2
(45) Date of Patent: *May 10, 2022

(54) SYSTEMS AND METHODS FOR CONTEXTUAL IMAGING WORKFLOW

(71) Applicant: Shenzhen Mindray Bio-Medical Electronics Co., Ltd., Shenzhen (CN)

(72) Inventors: Glen W. McLaughlin, San Carlos, CA (US); Ludwig Steffgen, Mainleus (DE); Anne Shelchuk, Mountain View, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 88 days.

This patent is subject to a terminal disclaimer.

(21) Appl. No.: 16/792,018

(22) Filed: Feb. 14, 2020

(65) Prior Publication Data

US 2020/0185094 A1 Jun. 11, 2020

Related U.S. Application Data

(63) Continuation of application No. 15/365,589, filed on Nov. 30, 2016, now Pat. No. 10,580,528, which is a
(Continued)

(51) Int. Cl.
*G01S 7/52* (2006.01)
*G06F 3/04842* (2022.01)
(Continued)

(52) U.S. Cl.
CPC .............. *G16H 40/63* (2018.01); *A61B 5/055* (2013.01); *A61B 6/032* (2013.01); *A61B 6/037* (2013.01);
(Continued)

(58) Field of Classification Search
CPC ......... A61B 5/055; A61B 6/032; A61B 6/037; A61B 6/4405; A61B 6/465; A61B 6/468;
(Continued)

(56) References Cited

U.S. PATENT DOCUMENTS 6,603,494 B1 * 8/2003 Banks .................... A61B 6/566
715/807
6,687,329 B1 * 2/2004 Hsieh .................... A61B 6/032
378/62
(Continued)

*Primary Examiner* — Jennifer N Welch
*Assistant Examiner* — Reji Kartholy
(74) *Attorney, Agent, or Firm* — Kory D. Christensen

(57) ABSTRACT

A hierarchical workflow is configured to associate examination information captured using an imaging platform with contextual metadata. The examination information may include ultrasound image data, which may be associated with annotations, measurements, pathology, body markers, and/or the like. The hierarchical workflow may comprise templates associated with respective anatomical regions, locations, volumes, and/or surfaces. A template may define configuration data to automatically adapt the imaging platform to capture imaging data in the corresponding anatomical region. The template may further include guidance information for the operator, including processing steps for capturing relevant examination information. Additional examination information may be captured and included in the hierarchical workflow.

25 Claims, 11 Drawing Sheets

Related U.S. Application Data continuation of application No. PCT/US2015/032287, filed on May 22, 2015.

(60) Provisional application No. 62/005,724, filed on May 30, 2014.

(51) Int. Cl.

| | | |
|---|---|---|
| *G16H 40/63* | (2018.01) | |
| *A61B 8/00* | (2006.01) | |
| *G16H 30/20* | (2018.01) | |
| *G16H 30/40* | (2018.01) | |
| *A61B 5/055* | (2006.01) | |
| *A61B 6/03* | (2006.01) | |
| *A61B 6/00* | (2006.01) | |
| *A61B 8/08* | (2006.01) | |

(52) U.S. Cl.
CPC ............ *A61B 6/4405* (2013.01); *A61B 6/465* (2013.01); *A61B 6/468* (2013.01); *A61B 6/5229* (2013.01); *A61B 8/4405* (2013.01); *A61B 8/461* (2013.01); *A61B 8/465* (2013.01); *A61B 8/467* (2013.01); *A61B 8/468* (2013.01); *A61B 8/5238* (2013.01); *G01S 7/52084* (2013.01); *G01S 7/52098* (2013.01); *G16H 30/20* (2018.01); *G16H 30/40* (2018.01); *A61B 8/462* (2013.01); *G06F 3/04842* (2013.01)

(58) Field of Classification Search
CPC ..... A61B 6/5229; A61B 8/4405; A61B 8/461; A61B 8/462; A61B 8/465; A61B 8/467; A61B 8/468; A61B 8/5238; G01S 7/52084; G01S 7/52098; G06F 3/04842; G16H 30/20; G16H 30/40; G16H 40/63

See application file for complete search history.

(56) References Cited

U.S. PATENT DOCUMENTS

| | | | |
|---|---|---|---|
| 6,904,161 B1* | 6/2005 | Becker | G16H 30/40 |
| | | | 382/128 |
| 6,944,330 B2 | 9/2005 | Novak et al. | |
| 8,699,823 B2 | 4/2014 | Boettger et al. | |
| 2001/0041992 A1* | 11/2001 | Lewis | G06Q 10/10 |
| | | | 705/3 |
| 2011/0028825 A1 | 2/2011 | Douglas et al. | |
| 2012/0172700 A1* | 7/2012 | Krishnan | G16H 30/20 |
| | | | 600/407 |
| 2012/0281904 A1 | 11/2012 | Gong et al. | |
| 2012/0310668 A1 | 12/2012 | Kotula et al. | |
| 2013/0102877 A1 | 4/2013 | Mori et al. | |
| 2013/0163838 A1 | 6/2013 | Barr et al. | |
| 2013/0343515 A1 | 12/2013 | Besson | |
| 2014/0104311 A1 | 4/2014 | Park et al. | |
| 2014/0164968 A1* | 6/2014 | Aalami | G16H 40/63 |
| | | | 715/771 |
| 2014/0180721 A1 | 6/2014 | Cheline et al. | |
| 2015/0169836 A1* | 6/2015 | Vahala | A61B 5/015 |
| | | | 600/407 |

\* cited by examiner

SYSTEMS AND METHODS FOR CONTEXTUAL IMAGING WORKFLOW

TECHNICAL FIELD

This application relates to ultrasound imaging and, in particular, to a hierarchical imaging workflow to generate contextual examination information.

DETAILED DESCRIPTION OF PREFERRED EMBODIMENTS

Figure 1:
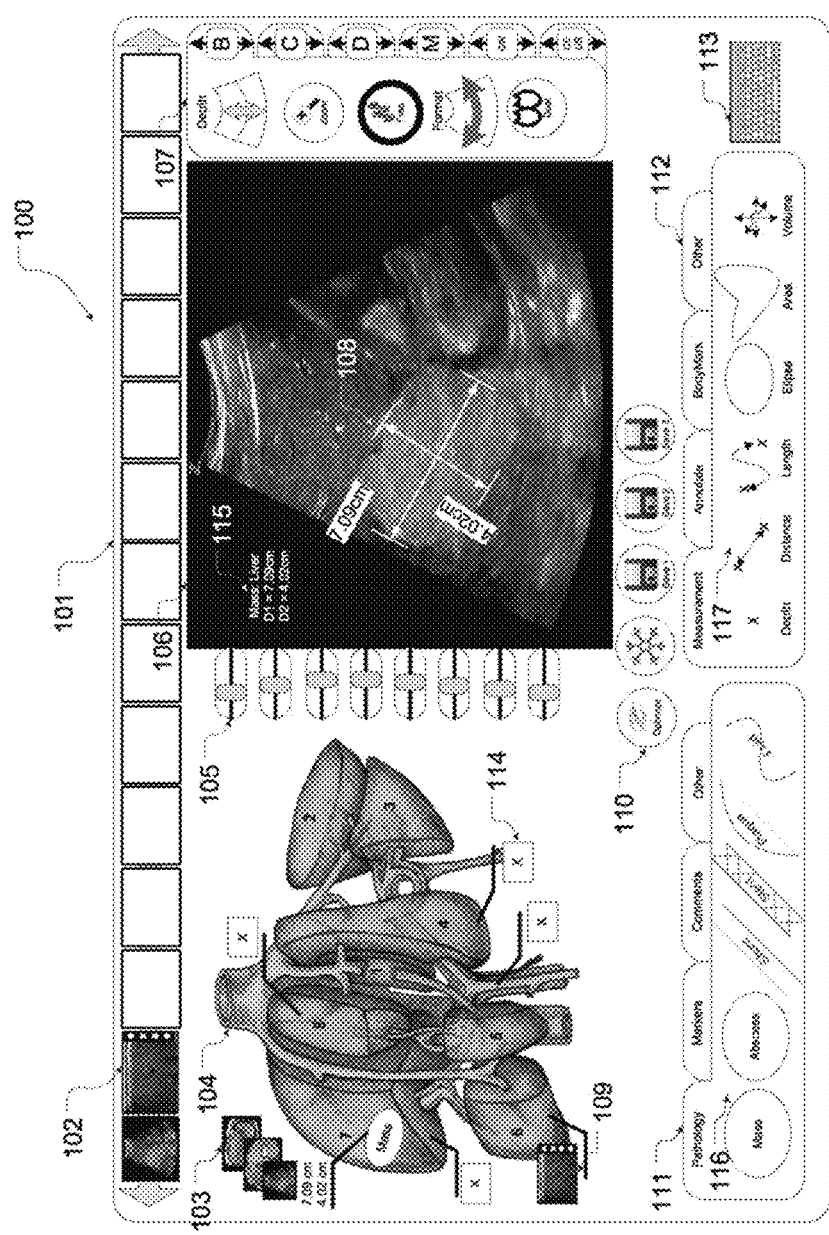
FIG. 1 depicts one embodiment of an interface for hierarchical workflow.

Diagnostic ultrasound imaging typically involves the acquisition of imagery data. The imagery data may be accompanied by metadata, such as annotations, measurements, and the like, which document certain results and/or findings pertaining to the imagery data. In some cases, annotations are applied directly to the images in order to, inter alia, enhance the viewer's understanding of the imagery data. The annotations may include, for example, a graphical body marker of the region being scanned and/or an indication of transducer placement.

Ultrasound examination procedures are typically focused on a single examination type. Although these types of procedures can be efficient in certain circumstances, deviations due to, inter alia, pathology and/or the need for additional information may not be well defined. In some instances, a "protocol" exam methodology is used to ensure a more consistent set of images and/or annotations. These protocols typically define linear steps for an exam, such as image capture, text annotation, measurements, and so on. Although such protocols can be efficient in certain situations, they lack the ability to provide additional exam context. For example, it may be difficult to call attention to anomalies, deviate from the prescribed steps in response to, inter alia, an observed pathology, and/or the like. Moreover, protocol exam methodologies do not define a hierarchical structure for information gathered in the exam.

Disclosed herein are embodiments of systems and methods for providing a hierarchical workflow for image-based examinations, such as ultrasound imaging. The disclosed systems and methods may provide a hierarchical context for an exam that a) defines efficient and consistent examination procedures and b) supports deviations from typical exams due to, inter alia, observed pathology and/or the need for additional information. The disclosed hierarchical workflow may define a unified context for seamlessly incorporating additional information gathering steps into existing exam, exam review, and/or documentation processes. The hierarchical workflow may also provide an improved way to understand the overall status of exam data in a graphically relevant manner, including, inter alia, the seamless incorporation of information from other exams, measurements or other modalities resulting in enhanced clinical utility, an overall hierarchical structure of the exam generated naturally during examination procedures, and the like.

In some embodiments, the disclosed hierarchical workflow may further comprise generating contextual information pertaining to an examination. As used herein, contextual information refers to examination data and associated contextual metadata that provides a context and/or relationship for the data. Contextual metadata may include, but is not limited to: information pertaining a particular anatomical region, location, and/or volume associated with the information, pathology information, patient information (e.g., name, identifier, and/or the like), patient history information (e.g., previously acquired imagery data), anatomical context, and/or the like. In some embodiments, contextual information may be associated with and/or tagged to entries of an anatomical index. As used herein, an "anatomical index" refers to an index and/or a map of anatomical locations, regions, and/or examination types. An anatomical index may comprise entries corresponding to anatomical regions, locations, surfaces and/or volumes capable of being scanned by one or more data capture platforms (e.g., cover a set of anatomical locations and/or regions capable of being scanned by an ultrasound imaging system). Contextual information may be associated with one or more entries of the anatomical index, which may define the anatomical region, location, volume, and/or surface associated with the information. For example, an image acquired by an ultrasound system may be associated with an entry of the anatomical index that defines the anatomical region corresponding by the imagery data. Alternatively, or in addition, contextual information may comprise other types of information, such as measurement information, annotations, patient information, patient history, and/or the like.

The contextual information and/or anatomical index disclosed herein may be stored and/or maintained in a data storage system such as a database (e.g., a relational database, an object-oriented database, an eXtensible Markup Language (XML) database, or the like), a directory, a file system, and/or the like, which may comprise and/or be embodied on a non-transitory, computer-readable storage medium, such as a hard disk, an optical storage medium, a solid-state storage medium (e.g., Flash storage media), and/or the like. The data storage system may be capable of associating data with contextual metadata, which may comprise associating imagery data with anatomical index information, annotations, measurements, patient information, related imagery data, and/or the like.

Figure 2:
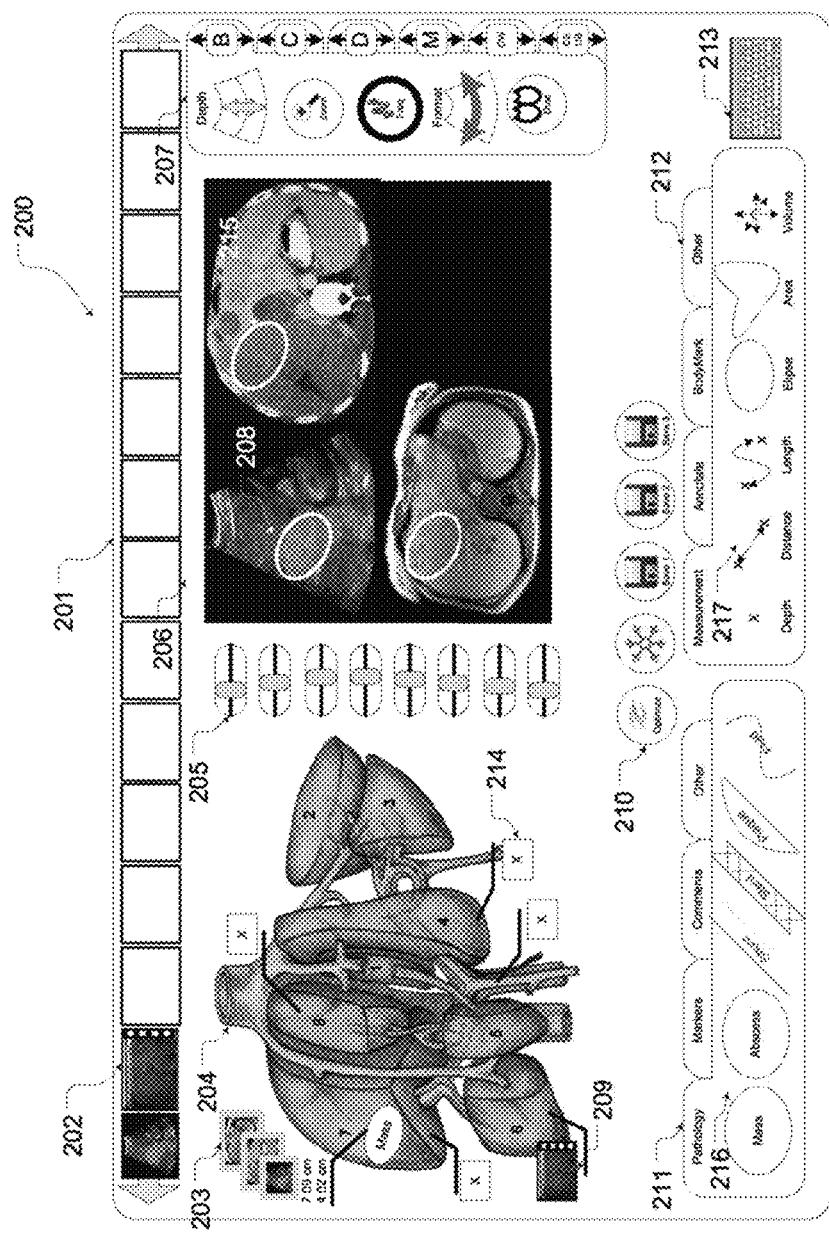
FIG. 2 depicts one embodiment of an interface for analysis of contextual information.

Contextual information pertaining to an examination may be filtered and/or refined to generate traditional examination report data, such as linear reports. Alternatively, or in addition, the contextual information may be visualized holistically in order to, inter alia, increase the overall utility of each source of information comprising the contextual information. In some embodiments, the contextual information may be visualized in an anatomically based dashboard pertaining to a particular area under investigation. Imagery data may, for example, be represented using thumbnail indicators overlaid on an anatomical model, as depicted in FIGS. 1 and 2. In other embodiments, historical information pertaining to a patient may be aggregated for presentation to a reviewing physician in order to, inter alia, track the progress of anomalies and/or the like over time.

The hierarchical workflow embodiments disclosed herein may capture contextual information by use of contextual examination templates (templates). As used herein, a "template" refers to a data set that defines examination procedures for a particular anatomical location, region, volume, surface and/or examination type. Accordingly, a template may be associated with and/or correspond to a particular entry of the anatomical index. A template may include, but is not limited to: configuration data, examination guidance information, and/or the like. The configuration data may comprise baseline configuration parameters for an examination platform (e.g., an image capture platform, such as an ultrasound system). The baseline configuration parameters for an ultrasound system may include, but are not limited to: frequency, depth, dynamic range, edge, tint, map, persistence, compounding, scan format, color box location/size/angle, color frequency, color gain, color persistence, color range, color map, spectral gate size, spectral gate position, spectral gate location, spectral gate angle, M-Mode cursor, M-Mode frequency, M-Mode location, M-Mode persistence, M-Mode tint, M-Mode dynamic range, M-Mode edge, and the like for other imaging modalities like Elastography, CEUS, 3D/4D, and/or the like. Further embodiments of systems and methods for configuring an imaging system are disclosed in U.S. Pat. No. 7,627,386 issued Dec. 1, 2009 to Larry Y. L. Mo et al., and which is hereby incorporated by reference.

The template may further comprise guidance information, which may be used to assist the operator of the image capture platform in performing an examination. The guidance information may include, but are not limited to, guidelines pertaining to annotations, measurement indicators, body markers, examination procedures (e.g., steps), and/or the like. The guidance information may be adapted for the anatomical location and/or examination type of the corresponding template and/or anatomical index.

The templates disclosed herein may correspond to the anatomical index. Accordingly, templates may be associated with respective sets of one or more entries of the anatomical index. The templates may be stored and/or maintained in a data storage system, such as a database, a directory, a file system, and/or the like, as disclosed herein. An operator may define templates by use of human machine interface (HMI) components of the imaging platform and/or other computing device. As used herein, HMI components may include, but are not limited to: virtual displays, touch inputs, keyboard inputs, audio inputs, audio outputs, haptic inputs, haptic outputs, keyboards, pointer input devices (e.g., a mouse), motion input device(s) (e.g., cameras), and/or the like. Defining a template may comprise: a) specifying an anatomical location, region, and/or examination type (e.g., selecting an entry of the anatomical index), b) defining baseline configuration parameters for an image capture platform, and/or c) specifying guidance information, such as annotations, measurement indicators, body markers, examination procedures (e.g., steps), and/or the like. Templates may be indexed by and/or tagged to a respective anatomical location, region, and/or examination type in the anatomical index, as disclosed herein. Accordingly, the anatomical region, location, and/or examination type associated with the template may be used as a "primary key" for the particular template within the anatomical index.

In some embodiments, an imaging platform comprises and/or is communicatively coupled to an anatomical index. An operator may select a template by use of one or more HMI components of the imaging platform and/or other computing device. In some embodiments, templates (and/or data of the templates) are displayed in a linear selectable manner on an interface of the imaging platform. Templates may be presented as a menu, a list, and/or the like. Alternatively, or in addition, templates may be displayed in a hierarchy based on the respective anatomical location, region, and/or examination type of the templates. In some embodiments, the operator may select a template by selecting a particular region, location, volume, and/or surface of the anatomical index (e.g., selecting a location within a graphical representation of the anatomical index). In response to selection of a template, the imaging platform may be automatically configured for examination of the corresponding anatomical region, location, volume, surface, and/or examination type, which may include, but is not limited to: a) configuring the imaging platform in accordance with the configuration data of the selected template, b) providing contextual guidance information of the selected template to the operator of the imaging platform, and/or c) associating data captured by the imaging platform with contextual information corresponding to the selected template (e.g., contextual information, such as the corresponding entry of the anatomical index).

As disclosed above, templates may be added to the anatomical index through, inter alia, the imaging platform. In some embodiments, new templates may be added during an ongoing examination. Templates may be added in a hierarchical fashion. For example, a new template may "inherit" information from a current and/or selected template (the "parent" template). The new template may, for example, inherit the anatomical region, location, examination type, configuration data, and/or contextual guidance from the parent template. The operator may override inherited data by, inter alia, entering information through, inter alia, HMI components of the imaging platform and/or other computing device.

Alternatively, or in addition, the operator may add examination steps while an examination is in process and/or based on prior patient knowledge. The additional examination steps may generate additional contextual information (e.g., additional imagery data, annotations, pathology indicators, measurements, and so on). The additional contextual information may be associated with the anatomical index, as disclosed herein. In some embodiments, the additional contextual information may be appended to the end of a linear based sequence defined by a template as "anomalies." As used herein an "anomaly" refers to contextual information acquired outside of a particular template (e.g., in addition to or in place of steps and/or procedures defined in a template). As disclosed above, an anomaly may occur in response to, inter alia, imagery data captured while performing the steps of a template. For example, an operator may take steps to capture additional imagery data in response to detecting a mass or tumor during a scan of a particular anatomical region. The imagery data corresponding to the additional operations may be associated and/or tagged with context metadata corresponding to the current template. Referring to the example above, the imagery data captured in response to detecting the mass or tumor during a scan of a patient's liver may be associated with and/or tagged with the contextual metadata of the liver scan template (e.g., may be associated with the liver in the anatomical index). Alternatively, or in addition, the operator may define contextual metadata by use of HMI components of the imaging platform, which may comprise specifying a location, region, volume, and/or surface pertaining to the additional information in a graphical representation of the anatomical index.

As disclosed above, capturing data using a hierarchical workflow as disclosed herein may comprise a) selecting a context for the data acquisition operation(s) by, inter alia, selecting a template and/or an entry of the anatomical index, which may automatically configure the data acquisition system (e.g., ultrasound system) in accordance with baseline parameters and/or provide contextual guidance to an operator of the data acquisition system, b) receiving data acquired by use of the data acquisition system, and c) storing the received data as contextual information on a non-transitory computer-readable storage medium. The contextual information may be generated by combining the acquired data with contextual metadata, such as anatomical location, region, volume, surface, examination type, and/or the like. The contextual information may further comprise measurements, annotations, pathology information, and/or the like.

In one exemplary embodiment, an operator may perform a liver examination by a) selecting a liver scan template, and b) performing data acquisition operations using an imaging platform, such as an ultrasound system. The ultrasound system may be automatically configured with baseline parameters of the selected liver examination template. The operator of the ultrasound system may capture imagery data, perform measurements, and enter annotations, as disclosed herein, which may be associated with contextual metadata and stored in a computer-readable storage medium. During the scan operation, the operator may notice an anomaly in the imagery data, such as a lesion. In response, the operator may generate a tag to describe the anomaly. As used herein, a "tag" refers to contextual information pertaining to captured imagery data, such as anatomical structure, characteristics, anomalies, and/or the like. The operator may capture information pertaining to the anomaly by, inter alia, positioning a mass/lesion widget of the ultrasound system at the appropriate anatomical location within the graphical representation of the imagery data and applying an anomaly tag to the contextual information pertaining to the examination (e.g., a "lesion tag"). Applying the anomaly tag may comprise associating the anomaly tag with the contextual metadata capturing during the scan using, inter alia, a relational data structure, as described herein (e.g., in a database, a directory, a file system, or the like). The anomaly may comprise contextual information including, but not limited to: the position of the anomaly (e.g., position relative to the anatomic index), a body marker, measurements, and/or the like. The operator may author additional descriptive metadata and/or fields of the tag. The operator may, for example, title the tag as a "liver lesion," which may provide additional context for the reviewing physician.

Although a particular example of a tag pertaining to anomaly data is described herein, the disclosure is not limited in this regard and could be adapted to generate new contextual information (e.g., tags) corresponding to any suitable feature, characteristic, pathology, and/or the like. For example, tags may be used to record new measurements and/or measurement types, which may be associated with contextual information captured during an examination using a relational data store, as described herein. The contextual information may be further configured to associate the contextual information captured in the scan with other complementary information from other modalities both diagnostic and therapeutic to be included. Tags and/or other contextual information may be presented in a hierarchical display interface. The hierarchical display interface may present imagery data based on acquisition location within the anatomical index, capture time, and/or the like. In some embodiments, the hierarchical display may comprise a history of contextual information pertaining to the patient (e.g., from prior exams). Referring to the exemplary liver lesion anomaly tag disclosed above, a history of contextual information pertaining to the patient may be presented to determine when the lesion first appeared and progressed over time.

As disclosed above, templates may define a series of data gathering steps to be completed by an operator of the imaging platform, which may include, but are not limited to: scanning particular anatomical regions, locations, volumes, and/or surfaces, performing one or more pre-determined measurements, entering one or more pre-determined annotations, and/or the like. The imaging platform may be configured to alert the operator of missing steps (if any) prior to completing the examination. Closing an examination may comprise storing contextual information acquired during the examination, including contextual information pertaining to anomalies (e.g., anomaly tags), in a data store. The contextual information may be associated with contextual metadata, as disclosed herein.

Contextual information stored in the data store may be made available to other computing devices by use of a network and/or other data sharing mechanism. Contextual information may be provided in one of a plurality of different formats and/or configurations. In some embodiments, a review station is configured to utilize contextual metadata to provide an anatomical based review of the imagery data, measurements, annotations, and the like. The revision station may provide for accessing imagery data using the anatomical index (e.g., by selecting areas on a graphical representation of the anatomical index). The review station may be further configured to display information pertaining to specific tags, such as captured images, annotations, measurements, pathologies, anomalies, images from complementary modalities, such as other ultrasound images, computed tomography (CT) images, positron emission tomography (PET) images, magnetic resonance imaging (MRI) images, x-ray images, and fluoroscopy images, corresponding measurements, annotations, calculations, and/or the like. Other review stations may provide reviewers with a more rudimentary, linear-type view of the contextual information. Alternatively, or addition, the contextual information may be presented as a visual map that associates the contextual information in order to, inter alia, present the anatomical index as a visual map and/or reference guide for the examination so that the reviewer can access a single image that represents the salient findings of the exam to identify where the reviewer's attention would be best used during review.

Upon completion of an examination, the corresponding contextual information may be stored in the data store, as disclosed above. Storing the contextual information may comprise writing entries into a relational database, directory, file system, and/or the like. The imaging system may be further configured to generate an examination report based on the stored contextual information. The report may comprise various forms of the contextual information to enable a reviewer to review the examination information, provide commentary, insert his or her professional diagnosis, and/or the like. In some embodiments, the reviewer may be given write access to the contextual information, which may comprise the ability to modify fields of the contextual information (e.g., annotations), such as a diagnosis field and/or the like. Information entered and/or modified by the reviewer may be stored with the contextual information in the data storage system, as disclosed herein.

FIG. 1 depicts one embodiment of an interlace 100 (a graphical user interface (GUI)) for utilizing a hierarchical, anatomical based workflow disclosed herein. The displayed region 101 contains the outline of the interface. The interface 100 of FIG. 1 may be configured for display on a computing device, such as an imaging system (e.g., an ultrasound system, not shown). The imaging system may comprise a processor, memory, a computer-readable storage medium, HMI components, image capture components, image processing components, and/or the like. The interface 100 and/or related processing functionality may be embodied as computer-readable instructions stored on a non-transitory computer-readable storage medium of the imaging system. The computer-readable instructions may be configured for execution by the processor of the imaging system to cause the imaging system to a) display the interface 100 on a display component (e.g., a monitor, a touchscreen, and/or the like), and/or b) implement image capture, processing, storage, and/or other functionality in response to manipulation of the inputs of the interface 100. In some embodiments, the imaging system comprises dedicated hardware components configured to display the interface 100 and/or implement corresponding functionality, which may include, but is not limited to, one or more: processors, field-programmable gate arrays (FPGAs), Application Specific Integrated Circuits (ASICs), Programmable Logic Controllers (PLCs), and/or the like.

The interface 100 may be accessible by HMI components of the imaging system. In the FIG. 1 embodiment, the interface 100 may be configured for use with one or more of: a multi-touch display device, a gesture-based display device, a hard key based input, a pointer-based input (e.g., mouse input), a combination of input mechanisms, and/or the like.

The interface 100 may comprise a sequential display component 102 configured to display a history of image capture data in a linear or sequential arrangement. The sequential display component 102 may, therefore, comprise a log of image capture operations ordered by time (or other ordering metric). The sequential display component 102 may be configured to display thumbnail images corresponding to captured images and/or clips (video data).

In some embodiments, the sequential display component 102 is configured to display guidance information to an operator of the imaging system. The guidance information may indicate a sequence of images the operator is to capture during a particular examination type and/or as part of an examination of a particular anatomical region, location, volume, and/or surface. The sequential display component 102 may be populated with guidance information of a template. The guidance information may be displayed as text entries in the sequential display component 102 that describe the image(s) to be captured. Alternatively, or in addition, the guidance information may comprise a pointer and/or link to the area of interest on the anatomical index display component 104 of the interface 100.

The hierarchical workflow disclosed herein may comprise a plurality of templates that are associated with respective anatomical areas and/or scan types and that comprise a) configuration data including baseline parameters for automatically configuring the imaging system and b) guidance information to assist the operator in performing one or more examination operations, such as image capture operations, annotation operations, measurement operations, and/or the like. The interface 100 may provide various mechanisms for selecting a template. In one embodiment, the operator may select a template by selecting empty space on the sequential display component 102. The empty space may be associated with a tag corresponding to a particular scan type and/or anatomical region (e.g., liver scan), associated with a template. In response to selection of such a tag, the interface 100 may cause the imaging system to invoke the corresponding template, which may comprise a) accessing the selected template in a data storage system, b) automatically applying configuration data of the selected template (e.g., baseline parameters) to the imaging system, and/or c) adapting the interface 100 to display guidance information of the selected template (e.g., annotation interface components, measurement components, body marker components, scan guidance information, and/or the like).

Alternatively, or in addition, the operator may select a template by use of the anatomical index display component 104. The anatomical index display component 104 may comprise a graphical representation of the anatomical index. The anatomical index display component 104 may comprise selectable regions (1-8) that correspond to respective anatomical regions, locations, volumes, and/or surfaces of the anatomical index (marked with anatomical region markers 114 in FIG. 1). As disclosed above, image data captured by the imaging system may be associated with contextual metadata, such as the corresponding anatomical area, annotations, measurements, and so on. The interface 100 may be configured to leverage the contextual information in order to, inter alia, display imagery data according to its anatomical context. As illustrated in FIG. 1, contextual information (e.g., imagery data) pertaining to various anatomical areas may be displayed as thumbnails on respective areas of the anatomical index display component 104. In the FIG. 1 embodiment, imagery data pertaining to the liver (study 103) has been captured and is represented as respective thumbnails associated with anatomical area 7 of the anatomical index display component 104. Other imagery data associated with other anatomical areas may be associated with respective areas of the anatomical index display component 104 (e.g., imagery data 109 associated with anatomical area 6). In FIG. 1, anatomical areas for which no contextual information has been captured are displayed with an "x." Alternatively, such areas may remain blank and/or may comprise empty space. In some embodiments, the anatomical index display component 104 may display guidance information of a template. For example, anatomical areas to be scanned may be marked with an "x" (or other indicator) to guide the operator to anatomical areas that must be scanned as part of a particular examination type.

The operator may select a particular area of the anatomical index display component 104 (an anatomical region marker 114), which may comprise selecting a template corresponding to the respective anatomical area. In response to selecting an anatomical region marker 114, the imaging system may a) access the corresponding template, b) apply configuration data of the template, and/or c) modify the interface 100 in accordance with guidance information of the template, as disclosed herein.

Selection of a template through empty space of the sequential display component 102 and/or anatomical index display component 104 may be adapted according to selection of a widget in any of the headers 111. For example, in the pathology tab 116 the mass modification widget could be used to generate a new set of contextual information (study 103) associated with a mass in the liver. Selection of the "mass" input on the pathology tab 116 may result in selection of a corresponding template specific to a) a scan of a particular anatomical area (e.g., liver 7) of b) a particular scan type (e.g., mass scan). The selected template may, therefore, comprise baseline parameters configured to a scan of the liver and that include annotations, measurements, widgets, and/or other guidance information specific to scanning a mass in the liver.

The set of contextual information pertaining to the mass (study 103) may, therefore, comprise contextual information that includes a set of imagery data with corresponding metadata, such as pathology information 115. As illustrated in FIG. 1, the contextual information of the study 103 is associated with a specific area of the anatomical index (e.g., within the liver 7), and may be associated with contextual information, such as a pathology type, a title, measurements, and/or the like. Contextual information pertaining to the study 103 (and/or other contextual information gathered during the examination) may be associated with the patient in the data storage system, which may enable the study 103 to be correlated with other data, such as MRI images, CT images, patient history information (e.g., previous scan data), and/or the like.

The interface 100 further comprises an imaging region 106 configured to display captured imagery data. Upon generating a new entry into the exam (e.g., capturing imagery data), the operator may label the image based on a selected pathology and/or other criterion. In the FIG. 1 embodiment, the imagery data display in the region 106 comprises a scan of the liver mass of the study 103 and, as such, is labeled and/or tagged with the "mass" pathology. As disclosed above, the selected pathology may determine a template for the scan operation(s), which may include guidance information for the operator, such as measurement, annotation, and/or other widgets. The operator may select a measurement widget from the image based modification section 112 under the measurement tab 117 to acquire measurements needed as part of the "liver mass" template.

Although FIG. 1 depicts a measurement widget using distance, other types of measurement widgets may be provided including, but not limited to: an ellipse, area, volume, and/or the like. The measurement widgets may be associated with respective templates, which may correspond to different pathology types, anatomical areas, and/or the like.

The measurements and other information pertaining to the mass may be associated with the corresponding image data and/or anatomical index entry as contextual metadata. The interface 100 may provide for entry of additional text-based annotations by use of HMI components of the imaging system (not shown). In the FIG. 1 embodiment, selecting the QWERTY icon 113 may invoke a touch screen text input used for entering text annotations. Image annotations may be depicted as floating elements on the image data that can be positioned at a desired location within the imaging region 106.

The interface 100 may further comprise imaging controls 107, which may provide access to fundamental image controls through gesture based inputs. For example, selecting the B icon and moving the finger up or down to the desired level may modify B-mode gain. Alternatively, imaging controls 107 may be implemented using fixed keys and/or other input mechanisms. Ultrasound is a technology where there is a potential for variations in the attenuation of tissue at different depths so an ability to modify the gain settings from some normal value is also provided by gain inputs 105. The gain inputs 105 comprise slider controls used to adjust the respective gains at corresponding vertical positions within the image. The gain inputs 105 may be adjusted manually and/or set based on user preference. Alternatively, or in addition, the gain inputs 105 may be set automatically using the optimize input 110. The other inputs may include, but are not limited to, a "freeze" image input and one or more save inputs. The save inputs may be used to store the image in association with a region, location, volume and/or surface of the anatomical index display component 104 and/or linear display component 102. Different save inputs (e.g., save 1, save 2, and save 3) may be configured to perform different types of save operations, such as save an image still, save a clip, print an image, and/or save a combination of image and clip. As disclosed above, saving imagery data may comprise storing the imagery data on a data storage system, such that the imagery data is associated with contextual metadata, such as patient information, anatomical area, annotations, metadata, and/or the like.

The input 114 may be used to associate the image with a particular anatomical location, region, volume, and/or surface of the anatomical index 104. Alternatively, an image may be associated with the anatomical index 104 by, inter alia, dragging the image to a particular region (1-8) of the index 104 and/or sequential region 102. Associating an image with the anatomical index 104 may comprise associating the image with a template, which may comprise updating the image with corresponding annotations, body markers, measurement data, and/or the like.

Saving image data may comprise generating a thumbnail representation corresponding to the image data, which may be displayed within the anatomical index display component 104 and/or sequential display component 102, as disclosed above. Thumbnails may be adapted to indicate if the imagery data is a still image or a clip as depicted in 109. Once the operator has completed the scans comprising the examination, the anatomical index display component 104 may be populated with a complete set of contextual information (e.g. images, measurements, annotations, anomalies, and so on). The interface 100 may, therefore, provide a simple graphical representation of all the pertinent information of the study in a single, easy to digest picture. The information display in the interface 100 may correspond to the relational information (contextual metadata) associated with the captured imagery data. As illustrated in FIG. 1, imagery data is depicted in association with respective anatomical areas (on the anatomical index display component 104). In addition, the imagery data is associated with a higher-level examination operation (study), including specified annotations, measurements, and/or the like. The contextual information is further leveraged to provide contextual information for the anomaly (liver mass) identified during the examination, such that contextual information pertaining to the anomaly is associated with the corresponding anatomical area, other scan information, patient historical information, and/or the like. As disclosed above, the contextual information of the examination may be stored in a data storage system, such that the imagery data is associated with its corresponding contextual metadata. The association between the imagery data and contextual metadata may facilitate physician review. For example, if multiple examinations of the patient had been performed at different times, the corresponding imagery data may be identified in the data storage system (based on patient identifier and/or other relational information) for comparison and/or analysis.

FIG. 2 depicts another embodiment of an interface 200 for reviewing contextual information. The interface 200 may be embodied as computer-readable instructions stored on a non-transitory computer-readable storage medium. The instructions may be configured for execution by a computing device to a) display the interface 200 on a display device and/or b) implement corresponding processing functionality. Alternatively, or in addition, the computing device may be configured to implement the interface 200 by use of dedicated hardware components, as disclosed above. The computing device may comprise a workstation, an imaging platform, an imaging system, and/or a general-purpose computing device.

The interface 200 comprises a display area 201 comprising a sequential display component 202 and anatomical index display component 204. A user may select imagery data from either component 202 and/or 204. Imagery data may be displayed in image display area 206. In the FIG. 2 embodiment, imagery data corresponding to the study 203 (liver mass) have been selected. The selected imagery data may be highlighted in the anatomical index display component 204 (and/or sequential display component 202). The interface 200 may be further configured to access other types of imagery data pertaining to the selected anatomical area, such as ultrasound, CT and/or MRI imagery data as depicted. The related imagery data may be identified by use of contextual metadata associated with the images (e.g., the images may be associated with the particular patient, pathology, and/or anatomical area) in the data storage system.

The interface 200 may comprise an area of interest inputs (measurement tab 217). The area of interest marked by an ellipse for the ultrasound image 208 could also be associated with the CT image 215. If additional modifications of the settings of the images were desired, the operator could, for example, adjust the gain of the ultrasound image via a set of sliders inputs 205. The operator may also adjust other image parameters, such as zoom, gain, and/or the like using inputs 207. The inputs 207 may be further configured to make adjustments to images collected from other modalities. The operator may adjust the properties of the image(s), automatically optimize image settings (using input 210), and/or save copies of the images.

The operator may modify contextual metadata pertaining to the imagery data, which may comprise a) modifying existing pathology information, b) removing pathology information, c) adding pathology information, and/or d) the like. In the FIG. 2 embodiment, the operator may associate a modification of an existing index point 214 on the anatomical index display component 204 through the anatomical tools 211 by use of the pathology modification widgets 216. The modified annotations on the image may be saved using input(s) of the interface 200, as disclosed herein. Additional image based tools 212 could also be applied to the image data. In one embodiment, the operator may use the ellipse measurement widget to add new measurements to the images. Text annotations may be added by use of the QWERTY icon 213 component, as described above. The image data depicted in both the sequential display component 202 and the anatomical index display component 204 may indicate general image format (e.g., through their thumbnail with a modification, for example, to indicate that the image stored in a particular index is a clip 209).

Figure 3:
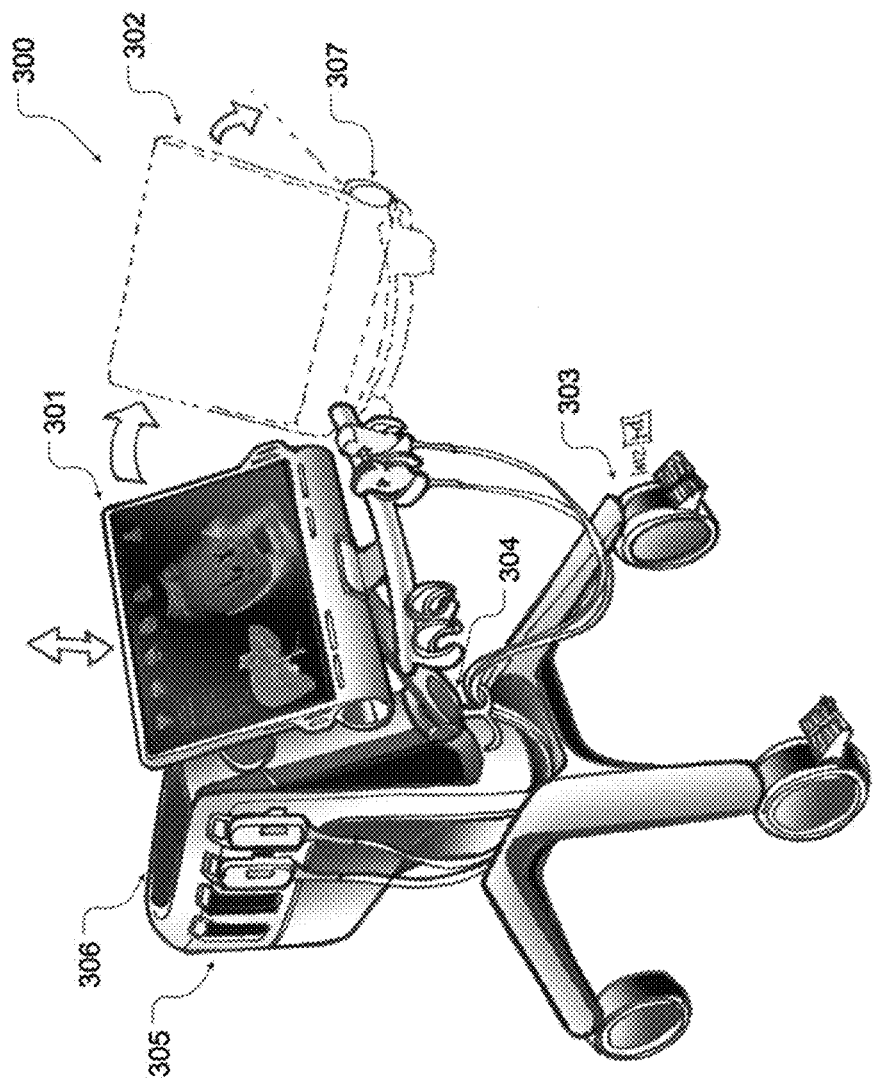
FIG. 3 depicts one embodiment of an imaging system.

FIG. 3 depicts another embodiment of an imaging system 300 comprising a mobile display 301. The mobile display 301 may be configured to display the interface(s) 100 and/or 200 disclosed herein. The imaging system 300 may comprise a processor, memory, and/or computer-readable storage medium. The imaging system 300 may further comprise a network interface, such as a wireless network transceiver, a wired network interface, and/or the like. The imaging system 300 may comprise and/or be communicatively coupled to a data storage system (not shown), which may comprise: a) an anatomical index, b) templates, and/or c) contextual information pertaining to one or more patients (e.g., historical examination data). The imaging system 300 may be configured to store imagery data and/or associated contextual metadata on the data storage system.

In the FIG. 3 embodiment, the interface may be adapted for display on a mobile computing device (mobile display 301). The mobile display 301 may comprise one or more of an LCD, an OLED, a PLASMA or the like. The mobile display 301 may include a touch panel capable of receiving touch inputs. The mobile display 301 may be positioned up, down, side-to-side (302), and so on. In order to provide the most convenient ergonomics, the mobile display 301 may be mounted on wheels 303 to assist with the movement and positioning of the imaging system 300. A convenient way to dress the transducer cable 304 along a path that will be associated with the display and convenient for the operator is also provided. There are multiple transducer connectors 305 so that the user can electronically select an active transducer without disrupting the exam. The imaging system 300 may also include a storage location 306 for an object, such as a printer, wipes, and/or the like. The imaging system 300 may further include a heated holding area 307 for acoustic gel.

Figure 4:
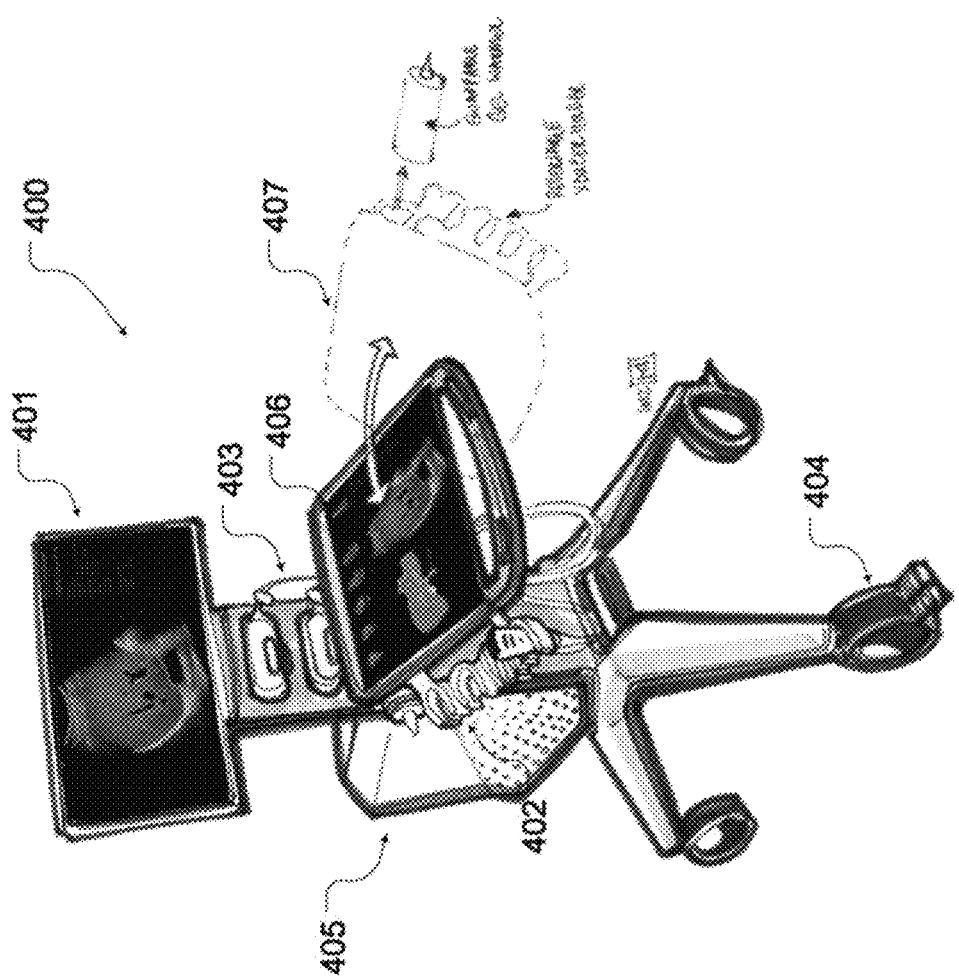
FIG. 4 depicts another embodiment of an imaging system.

FIG. 4 depicts another embodiment of an imaging system 400. The imaging system 400 may comprise one or more displays 401 and/or 406, which may be configured to display the interface(s) 100 and/or 200 disclosed herein. The imaging system 400 may comprise a processor, memory, computer-readable storage medium, network interface, and/or the like, as disclosed herein. The imaging system 400 may comprise and/or be communicatively coupled to a data storage system (not shown), which may comprise: a) an anatomical index, b) templates, and/or c) contextual information pertaining to one or more patients (e.g., historical examination data). The imaging system 400 may be configured to store imagery data and/or associated contextual metadata on the data storage system.

The imaging system 400 may comprise transducers 402 mounted along a main column 403 of the imaging system 400. The transducers 402 may be positioned to reduce cable drag and for operator ergonomics. The transducers 402 may be electronically selectable through an interface of the imaging system 400 to minimize the need for manual interchange during examination. The imaging system 400 may comprise lockable wheels 404.

The imaging system 400 may be configured to present an interface 406 on one or more of the displays 401 and/or 406 in accordance with the interface(s) 100 and/or 200 disclosed herein. The displays 401 and/or 406 may be configured to receive touch and/or gesture input. The display 406 may be repositioned 407 by an operator. The imaging system 400 may comprise a storage unit 405.

Figure 5:
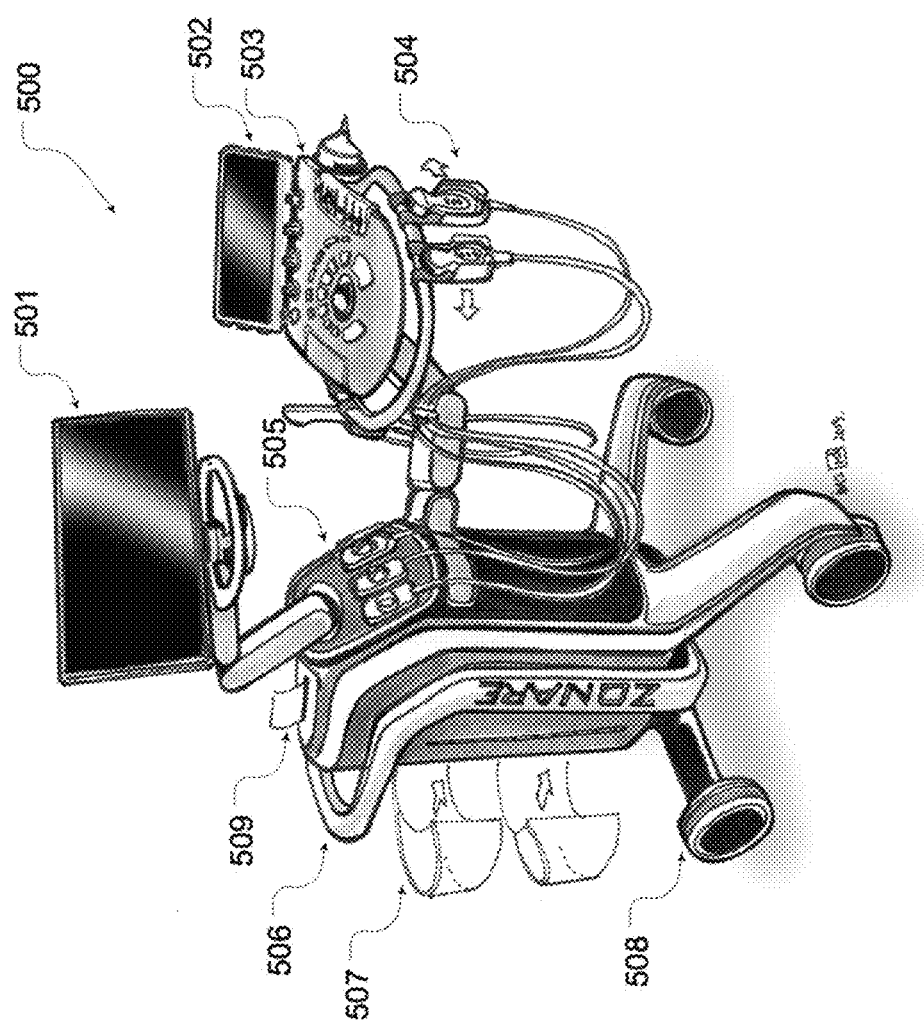
FIG. 5 depicts another embodiment of an imaging system.

FIG. 5 depicts another embodiment of an imaging system 500. The imaging system 500 may comprise a processor, memory, computer-readable storage medium, and/or network interface and may comprise and/or be communicatively coupled to a data storage system, as disclosed herein.

The imaging system 500 may comprise a primary display 501, which may be configured to display the hierarchical workflow interface 100 of FIG. 1 and/or the contextual review interface 200 of FIG. 2. The primary display 501 may, therefore, be configured to display image data captured by the imaging system 500 as well as the anatomical index display component 104 and/or 204. An operator may utilize input controls to manipulate the imaging system (e.g., control the hierarchical workflow), which may include touch screen inputs and/or HMI components (e.g., hard key inputs). The system may comprise additional peripheral units such as a warming gel holder 503, transducer holders 504, and/or the like. Components of the imaging system 500 may be configured for operation by either left or right hand. For example, gain correction controls (and/or other inputs) may be presented on either side of the display 502. The transducer connector ports 505 may be placed in a high and prominent position to allow maximum cable drape without reaching the floor. The imaging system 500 may comprise a push handle 506 to aid in positioning the imaging system 500 using, inter alia, the wheels 508. The imaging system 500 may further comprise storage 507 for supplementary equipment. The imaging system 500 may further include a printer 509.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

Figure 6:
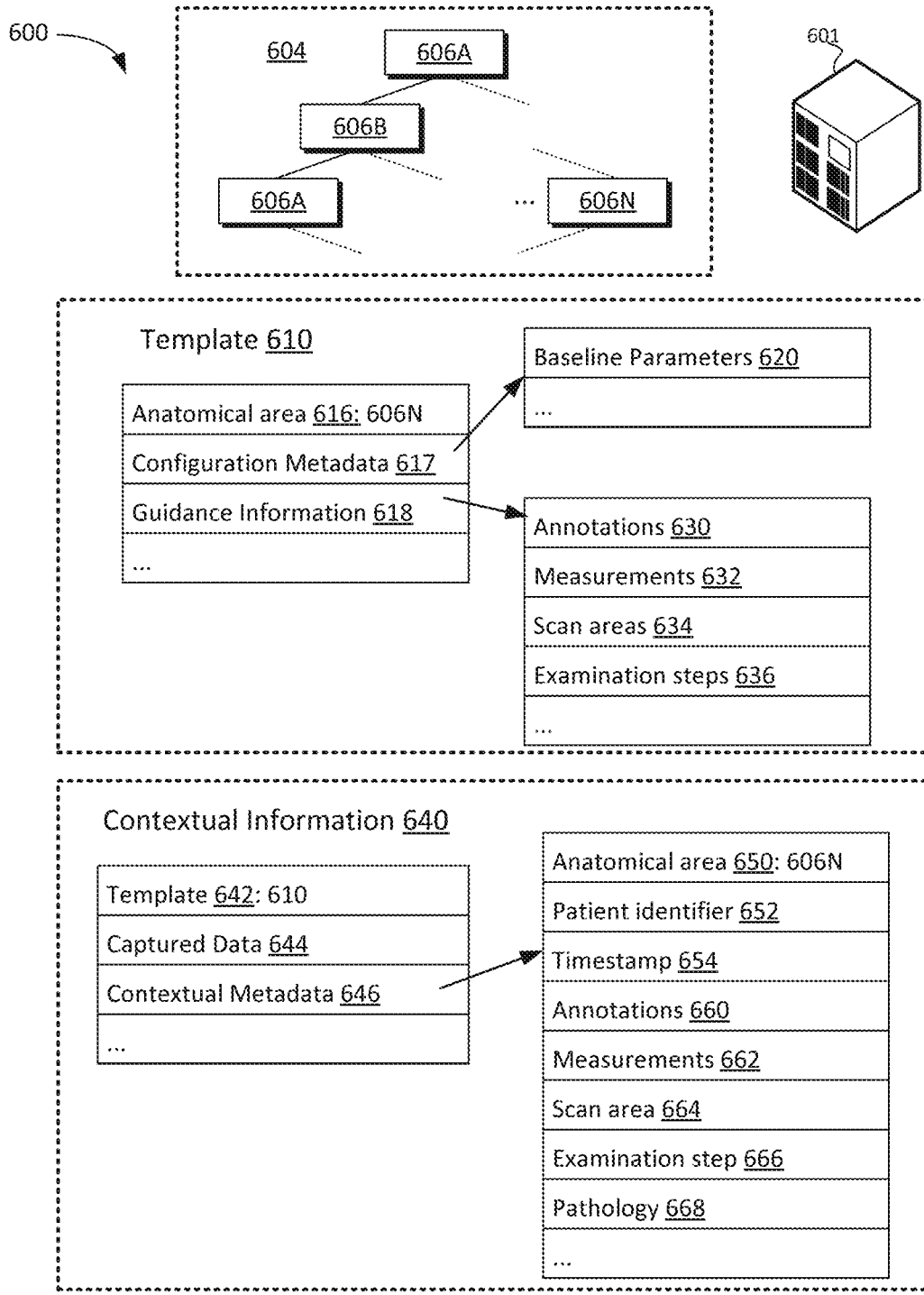
FIG. 6 depicts one embodiments of a data structures for capturing contextual information in a hierarchical workflow.

FIG. 6 depicts embodiments of data structures 600 for a hierarchical workflow. The data structures 600 of FIG. 6 and/or the other data structures disclosed herein, may be configured for storage in a data storage system 601, which may include, but is not limited to: a database, a directory, a file system, and/or the like. FIG. 6 includes an anatomical index 604 comprising entries 606A-N. The entries 606A-N of the anatomical index 604 may correspond to and/or represent anatomical areas, such as anatomical locations, regions, volumes, surfaces, structures, and/or the like. The entries 606A-N may be linked in a hierarchical data structure (e.g., a tree data structure) in accordance with anatomical relationships between the various entries. The entry 606B may, for example, correspond to the chest area, and the entry 606A may correspond to an anatomical area within the chest area (e.g., the heart).

The entries 606A-N of the anatomical index 604 may correspond to examination templates, such as the examination template 610. The examination template 610 may comprise a plurality of fields (e.g., entries, attributes, tables, and/or the like). In the FIG. 6 embodiment, the examination template data structure 610 comprises an anatomical area field 616 that associates the examination template 610 with one or more entries 610A-N of the anatomical index 604. In the FIG. 6 embodiment, the examination template 610 is associated with entry 606N of the anatomical index 604, which may correspond to the liver. The anatomical area field 616 may reference the entry 606N by use of a link, identifier, uniform resource locator (URL), relational database, and/or the like. As disclosed above, the template 610 may comprise configuration data 617 and/or guidance information 618. The configuration data 617 may include baseline parameters 620 and/or other configuration information related to a particular scan operation. The baseline parameters 620 may be maintained in a separate data structure (e.g., separate database table) and/or within a configuration data field 617 of the template data structure 610. The guidance information 618 may include, but is not limited to: annotation guidance information 630, measurement guidance information 632, scan area information 634, examination steps 636, and so on.

As illustrated in FIG. 6, the guidance information 618 may be maintained in one or more separate data structures. Alternatively, the guidance information 618 may be stored in a single entry, field, and/or table). As disclosed above, the annotation guidance information 630 may provide instructions to an operator on appropriate annotations for a particular type of image, examination-type, and/or the like. The measurement guidance information 632 may specify measurements to perform on imagery data captured during the examination. The measurement guidance information 632 may, for example, specify measurement widgets for display in the measurement tab 117 of the interface 100. The scan areas field 634 may identify imagery data to capture by one or more of: anatomical area, scan orientation, scan mode, and/or the like. The contents of the scan areas field 634 may be used to generate guidance information for display on the sequential display component 102 (e.g., empty space) and/or anatomical index display component 104 (e.g., anatomical region markers 114). The examination steps field 636 may specify scan and/or imaging steps.

As disclosed above, in response to selecting a template 610, the imaging system may be configured to automatically apply the configuration data 617 (e.g., baseline parameters 620) and/or modify the interface of the imaging system to include guidance information 618 of the template 610. Data captured during the examination process may be associated with the anatomical area 616 of the template 610 along with other contextual metadata.

FIG. 6 depicts one embodiment of a contextual information data structure 640 comprising data gathered during a hierarchical workflow. The contextual information may include, but is not limited to: a template field 642, a captured data field 644, contextual metadata field 646, and the like. The template field 642 may comprise a reference and/or link to a template associated with the contextual information 640 (e.g., the template used during capture of the corresponding image data). The captured data field 644 may comprise and/or reference data captured during examination, which may include but is not limited to: one or more images, video content, audio content, and/or the like. The contextual metadata 646 may comprise and/or reference descriptive metadata pertaining to the captured data 644, the contextual metadata 646 may include, but is not limited to: an anatomical entry 650 identifying the anatomical region, location, volume, and/or surface associated with the captured data 644 (e.g., entry 606N in the anatomical index 604), a patient identifier 652, a timestamp 654 corresponding to the date and/or time the corresponding data was captured, annotations 660, measurements 662, an indicator of the scan area and/or orientation 664, the examination step 666 associated with the captured data 644, pathology information 668 (diagnosis), and/or the like.

The association between the captured data 644 and the contextual metadata 646 may be used to aggregate imagery data captured at different times and/or using different modalities. For example, imagery data corresponding to the patient's liver may be identified by searching for contextual information 640 in the data storage system 601 tagged with a particular patient identifier (patient identifier field 652) that covers a particular anatomical area (based on the anatomical area field 650).

Figure 7:
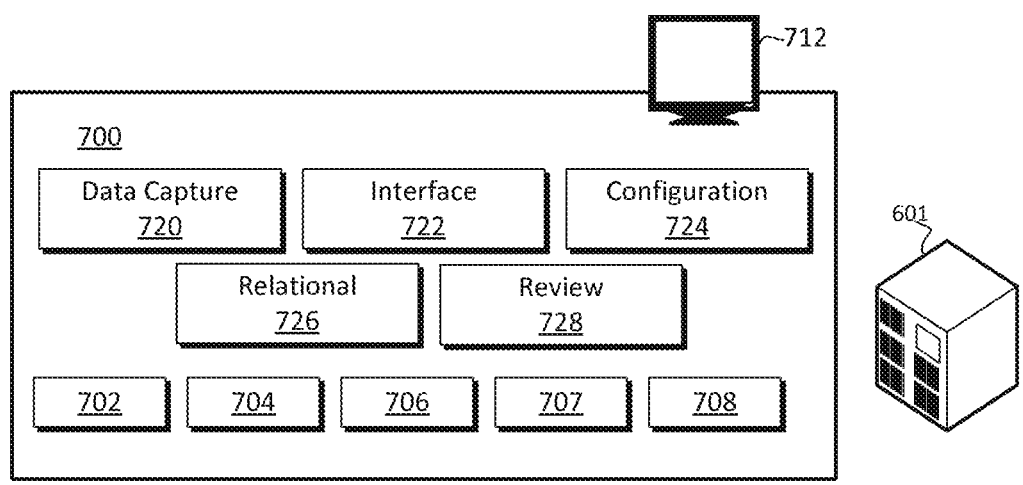
FIG. 7 is block diagram of one embodiment of a hierarchical workflow system.

FIG. 7 is a block diagram of one embodiment of an imaging system 700 configured to capture contextual information using a hierarchical workflow. The imaging system 700 may comprise a processor 702, memory 704, non-transitory, computer-readable storage 706, HMI components 707, and/or a network interface 708, as disclosed herein. The imaging system 700 may further include and/or be communicatively coupled to a data storage system 601. The data storage system 601 may comprise an anatomical index 604, templates 610, and/or contextual information 640, as disclosed herein.

The imaging system 700 may comprise a data capture module 720 comprising one or more data capture devices, such as ultrasound transducers. The image capture module 720 may be configured to capture imagery data pertaining to various anatomical areas of a patient.

The imaging system 700 may further comprise an interface module 722 configured to present an interface on a display 712 of the imaging system 700. The interface module 722 may be configured to present the interface 100 on the display 712. An operator may perform a scan operation by a) selecting a template through the interface 100 and b) performing the image capture operations of the template. Selecting the template may comprise selecting an anatomical area on the anatomical index display component 104 of the interface 100, selecting an empty space on the serial display component 102, a menu selection, and/or the like. In response to selection of a template, a configuration module 724 of the imaging system 700 may a) access the template data structure 610 from the data storage system 601 and b) automatically configure the imaging system 700 in accordance with the configuration data 617 of the selected template (e.g., apply the baseline parameters 620). The configuration module 724 may be further configured to modify the interface 100 in accordance with guidance information 618 of the template 610 which may include, but is not limited to: annotation guidance 630, measurement guidance 632 (e.g., widgets), scan area guidance 634, examination step guidance 636, and so on.

After selection of the template 610, the operator of the imaging system 700 may capture imagery data, enter annotations, perform measurements, and so on (in accordance with the guidance information 618). The operator may select a save input through the interface 100. In response, a relational module 726 of the imaging system 700 may be configured to a) associate imagery data captured by the imaging system 700 with contextual metadata associated with the template 610 and/or entered by the operator (e.g., anatomical area, patient identifier, timestamp, annotations, measurements, scan area, examination step, pathology, and so on), such that the captured data 644 is stored with the corresponding contextual metadata. The relational module 726 may be configured to store the captured data 644 in a contextual information data structure 640, as disclosed above (by use of the data storage system 601).

As disclosed above, the operator may deviate from predetermined steps of a template 610 in response to an anomaly (e.g., in response to detecting a mass in the patient's liver). Data captured during such a deviation may inherit the contextual metadata associated with the template 610 including, but not limited to: anatomical area 650, patient identifier 652, timestamp 654, and so on. The "anomalous" entry may, therefore, include contextual information that associates the captured data 644 with a particular patient, scan area (anatomical area), and/or the like. Contextual information pertaining to the anomalous entry may be stored in the data storage system 601 in association with contextual metadata by use of the relational module 726, as disclosed above.

The imaging system 700 may further comprise a review module 728 configured to aggregate data in the data store 601 based on contextual metadata associated with the data. The review module 728 may be configured to aggregate imagery data by, inter alia, searching for contextual information data structures 640 pertaining to a particular patient identifier 652 that correspond to a particular anatomical area 650, and/or the like. The review module 728 may be configured to display aggregate contextual information in on the display 712 by use of the interface module 722 (e.g., in the interface 200 of FIG. 2). The review module 728 may be further configured to provide for modification, removal, and/or addition of contextual metadata during review (e.g., modify, add, and/or remove annotations, measurements, diagnosis, and/or the like).

Figure 8:
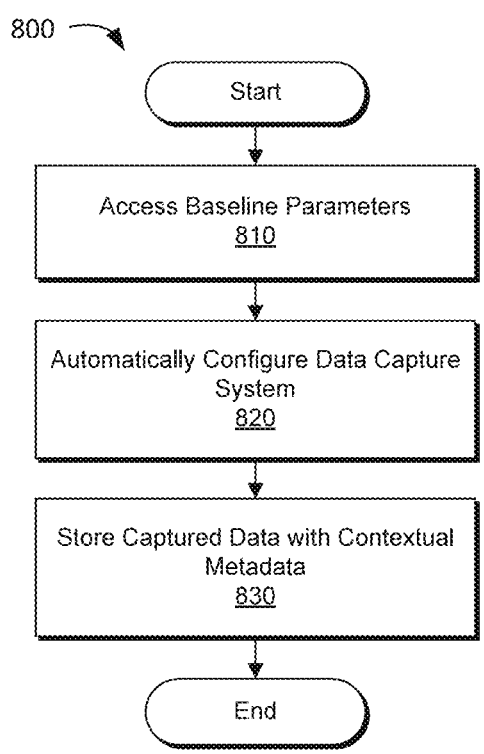
FIG. 8 is a flow diagram of one embodiment of a method for hierarchical workflow.

FIG. 8 is a flow diagram of one embodiment of a method 800 for a hierarchical workflow. The method 800 and/or the other methods, processes, and/or operations disclosed herein may be embodied as computer-readable instructions stored on a non-transitory computer-readable storage medium, such as the computer-readable storage 706 of the imaging system 700. The instructions may be configured for execution by a processor of a computing device to perform one or more of the steps of the method 800 (e.g., processor 702 of the imaging system 700). Alternatively, or in addition, steps of the method 800 (and/or other methods disclosed herein) may be implemented by use of hardware components, such as data storage systems 601, application-specific processing elements, and/or the like.

Step 810 may comprise accessing baseline configuration parameters for an imaging system 700. The baseline parameters of step 810 may be accessed in response to selection of a template 610, as disclosed herein. Step 810 may, therefore, comprise receiving a selection of a template through an interface 100 (e.g., selection of an anatomical area on the anatomical index display component 104, selection of empty space on the serial display component 102, a menu selection, and/or the like). Step 810 may further comprise accessing a template data structure 610 in a data storage system 601. The template data structure 610 may be associated with an entry 606A-N of an anatomical index 604.

Step 820 may comprise automatically configuring the imaging system 700 in accordance with the baseline parameters of step 810 (by use of, inter alia, a configuration module 724). As disclosed above, step 820 may comprise applying baseline parameters 620 of a selected template data structure 610. The template data structure 610 may further comprise guidance information 618. In some embodiments, step 820 further comprises configuring the interface 100 of the imaging system 700 in accordance with the guidance information 610, which may include annotation guidance 630, measurement guidance 632 (e.g., measurement widgets), scan area guidance 634, examination step guidance 636, and so on.

Step 830 may comprise storing data captured using the imaging system 700 as configured in step 820. Step 830 may comprise a) capturing imaging data using the imaging system 700 and/or b) entering contextual metadata pertaining to the captured data, such as annotations, measurements, diagnoses, and/or the like. Step 830 may comprise storing the captured data such that the data is associated with the corresponding contextual metadata (e.g., in a contextual information data structure 640, as disclosed herein).

Figure 9:
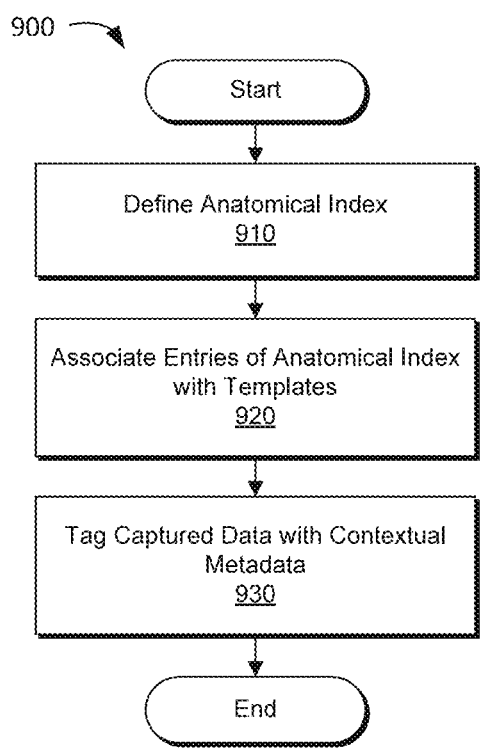
FIG. 9 is a flow diagram of another embodiment of a method for hierarchical workflow.

FIG. 9 is a flow diagram of another embodiment of a method 900 for a hierarchal workflow. Step 910 may comprise defining an anatomical index 604 comprising a plurality of entries 606A-N. The anatomical index 604 may correspond to anatomical regions, locations, volumes, surfaces, and/or structures capable of being scanned by one or more data capture systems. The anatomical index 604 may be stored in a data storage system 601 and/or in a memory and/or storage medium of an imaging system.

Step 920 may comprise associating entries 606A-N of the anatomical index 604 with template data structures 610. As disclosed herein, a template data structure 610 may correspond to one or more entries of the anatomical index 604 such that selection of the corresponding anatomical region, location, volume, surface, and/or structure results in applying the corresponding template data structure 610 to the imaging system 700. The template data structures 610 may be associated with entries 606A-N of the anatomical index 604 by use of a relational data storage system, such as a database, directory, file system, and/or the like.

Step 920 may further comprise defining configuration metadata for the template data structures 610. As disclosed herein, the configuration metadata 617 may be used to configure the imaging system 700 to capture image data of the anatomical area(s) associated with the template data structure 610. The configuration metadata may comprise baseline parameters 620 to configure data capture module 720 of the imaging system 700 (e.g., ultrasound transducers).

Step 920 may further comprise defining guidance information 618 for the template data structure 610. As disclosed herein, the guidance information 618 may comprise annotation guidance 630, measurement guidance 632 (e.g., define measurement widgets), scan area guidance 634, examination step guidance 636, and so on. The guidance information 618 may be adapted for display on an interface 100 of the imaging system 700, as disclosed herein.

Step 930 may comprise tagging data captured by use of a particular template data structure 610 with contextual metadata of the template data structure 610. Step 930 may comprise associating captured data with an anatomical area (e.g., an entry 606A-N of the anatomical index 604), a timestamp 654, annotations 660, measurements 662, scan area information 664, examination step information 666, pathology information 668 (e.g., diagnosis), and/or the like. Step 930 may be applied to data captured as part of an examination step 636 of the template data structure 610 and/or to data captured outside of the pre-defined steps (e.g., data captured in response to an anomaly). Step 930 may further comprise storing the captured data in association with the contextual metadata in the data storage system 601 (e.g., as contextual information data structures 640).

Figure 10:
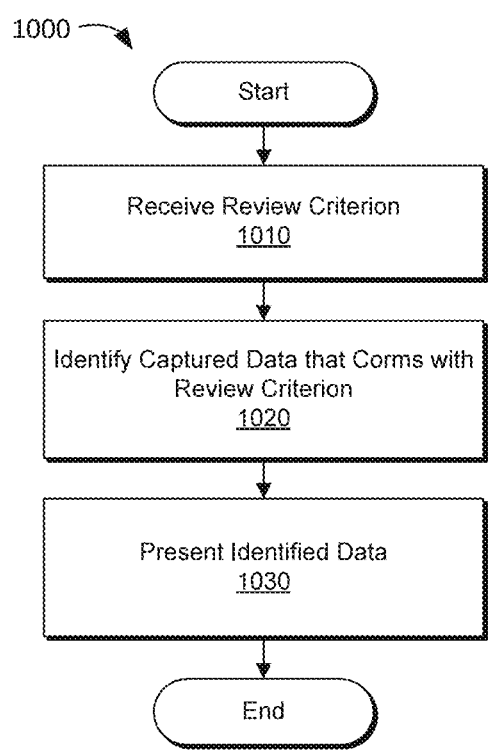
FIG. 10 is a flow diagram of another embodiment of a method for hierarchical workflow.

FIG. 10 is a flow diagram of another embodiment of a method 1000 for a hierarchal workflow. Step 1010 may comprise receiving review criterion from an operator. The review criterion may be received through an interface 200 of a computing device. The review criterion may correspond to contextual metadata 646 associated with captured data 644 of one or more contextual information data structures 640. The contextual information data structures 640 may be maintained in a data storage system 601, which may include, but is not limited to: a database, directory, file system, and/or the like. The review criterion may specify patient identifier(s) 652, anatomical area(s) 650, annotation(s) 660, measurement(s) 662, scan area(s) 664, examination step(s) 666, pathology information 668 (e.g., diagnosis), and/or the like. The review criterion may be adapted to aggregate imagery data pertaining to a particular anatomical area, a particular pathology, and/or the like. The review criterion may be configured to aggregate imagery data of different types and/or imagery data acquired at different times.

Step 1020 may comprise identifying contextual metadata data structures 640 that correspond to the review criterion of step 1010. Step 1020 may comprise searching the data storage system 601 using portions of the review criterion. Step 1020 may comprise aggregating a plurality of matching contextual information data structures 640 into a results set.

Step 1030 may comprise presenting the contextual information identified in step 1020 on a display (e.g., in the interface 200 disclosed herein). Step 1030 may comprise combining imagery data from a plurality of different contextual information data structures 640, editing fields of the contextual information data structures 640, and so on.

Figure 11:
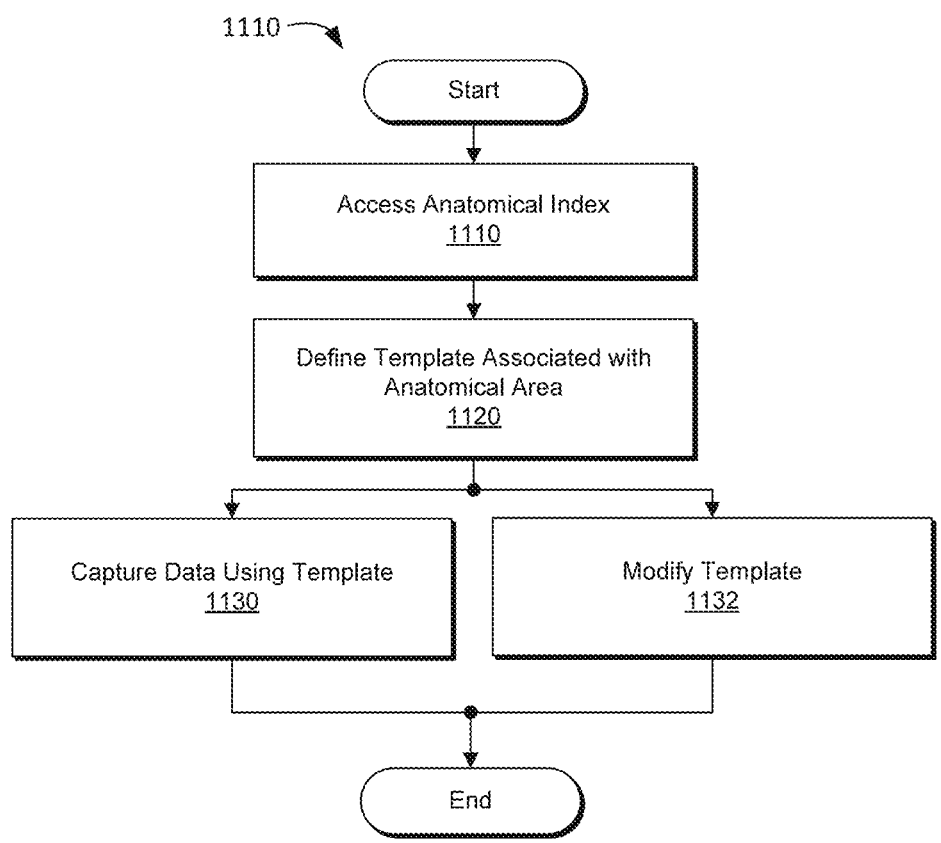
FIG. 11 is a flow diagram of another embodiment of a method for hierarchical workflow.

FIG. 11 is a flow diagram of another embodiment of a method 1100 for a hierarchical workflow. Step 1110 may comprise accessing an anatomical index 604, which may comprise accessing and/or referencing an embodiment of the anatomical index 604 as a data structure maintained in a data storage system 601 and/or a computer-readable storage medium of a computing device (e.g., imaging system 700). The anatomical index 604 may comprise entries 606A-N corresponding to anatomical areas, such as anatomical locations, regions, volumes, surfaces, structures, and/or the like.

Step 1120 may comprise defining a template 610 (e.g., defining data comprising a template 610 data structure as depicted in FIG. 6). As disclosed herein, a template 610 may be associated with an anatomical area. Step 1120 may, therefore, comprise associating the template 610 with one or more entries 606A-N of the anatomical index 604 of step 1110. Step 1120 may further comprise defining one or more of: configuration metadata 617 and/or guidance information 618 for the template 610. As disclosed herein, configuration metadata 617 may comprise baseline parameters 620 adapted to configure an imaging system 700 to capture imaging data pertaining to the anatomical area associated with the template 610. The baseline parameters 620 may comprise settings for an ultrasound imaging system and/or other data capture system (e.g., MRI, CT, PET, and/or the like). The guidance information 618 may include, but is not limited to: annotation guidance 630, measurement guidance 632 (e.g., measurement widgets), scan area guidance 634, examination step guidance 636, and/or the like. The guidance information 618 may be presented to an operator of the imaging system 700 on an interface 100 on a display 712 of imaging system 700 (e.g., by use of an interface module 722).

Step 1120 may be implemented using the interface 100 of the imaging system 700 (and/or other interface components). Alternatively, or in addition, step 1120 may occur on a workstation (e.g., a general-purpose computing device). Step 1120 may further comprise transmitting data of the template 610 to a data storage system 601 and/or an imaging system 700.

Step 1130 may comprise capturing data using the template 610 defined in step 1120. Step 1130 may include a) receiving a selection of the template 610 through the interface 100 of the imaging system 700 (e.g., selection of an area on the anatomical index display component 104 and/or serial display component 102) and/or b) receiving a selection of the template 610 through standard interface components, such as a menu, list, and/or the like on the imaging system 700 and/or other computing device. Step 1130 may further comprise accessing the template 610 in the data storage system 610 and/or computer-readable storage 706 of the imaging system 700 and/or automatically applying configuration metadata 617 and/or guidance information 618 of the template 610. Applying the configuration metadata 617 may comprise applying the baseline parameters 620 of the template 610 to the data capture module 720 of the imaging system 700 by use of the configuration module 724. Applying the guidance information 618 may comprise modifying the interface 100 presented on the display 712 of the imaging system 700, as disclosed herein. Step 1130 may further comprise tagging and/or associating data captured by the imaging system with contextual metadata defined in the template 610, such anatomical information, annotations, measurements, and so on.

Step 1132 may comprise modifying the template 610. Step 1132 may comprise modifying one or more of the anatomical area(s) 616 associated with the template 610, modifying the configuration metadata 617, and/or guidance information 618. Step 1132 may comprise modifying the scan areas 634 and/or examination steps 636 of the template 610. Step 1132 may be performed during image capture (e.g., during examination) and/or at another time. Moreover, the modifications of step 1132 may be implemented on the imaging system 700 or workstation.

In one embodiment, an operator may modify the template 610 in response to detecting an anomaly in captured imagery data during an examination (e.g., identifying a mass or lesion) by: a) adding further scan areas 634 and/or examination step 636 to capture additional information pertaining to the anomaly. In another embodiment, an operator may modify the template 610 in response to changes in best practices for a particular examination type, which may comprise adding, modifying, and/or removing one or more scan areas 634 and/or examination steps 636 of the template 610. Step 1132 may further comprise storing the modified template 610 in the data storage system 601 and/or computer-readable storage 706 of the imaging system 700.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

This disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element. The scope of the present invention should, therefore, be determined by the following claims:

The invention claimed is:

1. A method, comprising:
    displaying an anatomical index including an anatomical model of a plurality of anatomical areas of a patient, each anatomical area being associated with an examination template comprising:
        a hierarchical examination workflow defined by a plurality of examination procedures specific to a respective anatomical area, the hierarchical examination workflow specifying a set of image scans to be performed within the respective anatomical area; and
        baseline configuration parameters to be used by an imaging system when performing the set of image scans within the respective anatomical area;
    receiving a selection of an examination template in response to a user selection of an anatomical area from the anatomical model;
    accessing the hierarchical examination workflow and the baseline configuration parameters corresponding to the selected examination template, wherein the hierarchical examination workflow is adjustable during imaging of the selected anatomical area to modify the plurality of examination procedures defining the hierarchical examination workflow;
    automatically configuring the imaging system with the baseline configuration parameters from the selected examination template;
    storing image data of the selected anatomical area captured by use of the imaging system according to the hierarchical examination workflow on a storage system, such that the image data is associated with the selected anatomical area; and
    displaying thumbnails of the image data next to respective areas of the anatomical model corresponding to anatomical areas of the patient where the image data was captured by the imaging system.

2. The method of claim 1, wherein the storage system comprises a relational database and wherein the image data is associated with the selected anatomical area in the relational database.

3. The method of claim 1, wherein the selected anatomical area corresponds to one or more of an anatomical location, an anatomical structure, and an anatomical volume.

4. The method of claim 1, wherein the examination template comprises guidelines defining one or more image measurements to be performed.

5. The method of claim 4, further comprising updating the anatomical index in response to the guidelines of the selected examination template.

6. The method of claim 1, further comprising associating an additional image scan with contextual metadata corresponding to the examination template, wherein the additional image scan is not included in one or more image scans of the examination template.

7. The method of claim 1, further comprising:
    modifying the selected examination template according to adjustments of the hierarchical examination workflow; and
    writing the modified examination template to a storage system.

8. The method of claim 7, wherein the examination template is modified during an examination of the anatomical area.

9. The method of claim 7, wherein the examination template is modified by use of a workstation that is separate from the imaging system.

10. The method of claim 1, further comprising correlating the stored imaged data with external image data pertaining to the anatomical area associated with the stored image data, wherein the external image data comprises one of an ultrasound image, a computed tomography image, a positron emission tomography image, a magnetic resonance imaging image, an x-ray image, and a fluoroscopy image.

11. The method of claim 1, further comprising:
    displaying an indication in association with each anatomical area of the anatomical index for which image data has not been captured, the indication comprising a guide to an operator to anatomical areas that must be scanned as part of a particular examination type.

12. The method of claim 1, wherein the captured image data comprises a still image.

13. The method of claim 1, wherein the captured image data comprises a video clip.

14. The method of claim 1, wherein the captured image data is associated with contextual metadata including one or more of an indication of an anatomical area, an annotation, and a measurement.

15. The method of claim 1, wherein the thumbnails are overlaid upon the anatomical model.

16. An apparatus, comprising:
an interface module configured to display an anatomical index including an anatomical model of a plurality of anatomical areas of a patient, each anatomical area being associated within a data storage system with an examination template comprising:
a hierarchical examination workflow defined by a plurality of examination procedures specific to a respective anatomical area, the hierarchical examination workflow specifying a set of image scans to be performed within the respective anatomical area; and
baseline configuration parameters to be used by an image capture device when performing the set of image scans within the respective anatomical area;
the interface module being further configured to receive a selection of an examination template in response to a user selection of an anatomical area from the anatomical model and access the hierarchical examination workflow and the baseline configuration parameters corresponding to the selected examination template;
wherein the hierarchical examination workflow is adjustable during imaging of the selected anatomical area to modify the plurality of examination procedures defining the hierarchical examination workflow;
wherein the image capture device is automatically configured with the baseline configuration parameters from the selected examination template, the image capture device being configured to capture image data for the selected anatomical area according to the hierarchical examination workflow; and
a storage module configured to store the captured image data with contextual metadata that associates the captured image data with the selected anatomical area,
wherein the interface module is further configured to display thumbnails of the captured image data next to respective areas of the anatomical model corresponding to anatomical areas of the patient where the image data was captured by the image capture device.

17. The apparatus of claim 16, wherein the data storage system comprises a relational database.

18. The apparatus of claim 17, wherein the examination template comprises guidance information for performing the examination procedures, wherein the interface module is configured to adapt a measurement widget of a graphical user interface of the image capture device in accordance with the guidance information.

19. The apparatus of claim 18, wherein the guidance information identifies a plurality of scan areas, and wherein the interface module is configured to display indications of the scan areas on the anatomical index.

20. The apparatus of claim 17, wherein the templates are associated with respective entries of the anatomical index.

21. The apparatus of claim 16, wherein the storage module is to associate image data corresponding to an anomaly with an anatomical area associated with the selected examination template.

22. A system, comprising:
a processor and a computer-readable storage medium, the computer-readable storage medium comprising instructions that, when executed by the processor, cause the processor to perform operations, comprising:
displaying an anatomical index including an anatomical model of a plurality of anatomical areas of a patient, each anatomical area being associated with an examination template comprising:
a hierarchical examination workflow defined by a plurality of examination procedures specific to a respective anatomical area, the hierarchical examination workflow specifying a set of image scans to be performed within the respective anatomical area; and
baseline configuration parameters to be used by an image capture device when performing the set of image scans within the respective anatomical area;
receiving a selection of an examination template in response to a user selection of an anatomical area of the anatomical model and access the hierarchical examination workflow and the baseline configuration parameters corresponding to the selected examination template;
wherein the hierarchical examination workflow is adjustable during imaging of the selected anatomical area to modify the plurality of examination procedures defining the hierarchical examination workflow;
wherein the image capture device automatically applies the baseline configuration parameters associated with the selected examination template and captures image data for the selected anatomical area according to the hierarchical examination workflow; and
wherein the processor is further configured to display thumbnails of the captured image data next to respective areas of the anatomical model corresponding to anatomical areas of the patient where the image data was captured by the image capture device.

23. The system of claim 22, wherein the image capture device comprises an interface module configured to display one or more of annotation guidance, measurement guidance, scan area guidance, and examination step guidance for the selected examination template.

24. The system of claim 22, wherein the image capture device comprises a relational module configured to associate captured image data with the selected anatomical area associated with the selected examination template in the data storage system.

25. The system of claim 22, further comprising a review module configured to aggregate image data associated with contextual metadata that conforms to a review criterion.

* * * * *